US006595922B1

(12) United States Patent
Henderson et al.

(10) Patent No.: US 6,595,922 B1
(45) Date of Patent: Jul. 22, 2003

(54) MEDICAL DIAGNOSTIC ULTRASOUND IMAGING SYSTEM WITH AN AMBIENT ROOM LIGHT

(75) Inventors: Richard W. Henderson, Fremont, CA (US); David E. Burris, Santa Cruz, CA (US); Jeffrey N. Gamelsky, Palo Alto, CA (US); Malachy Sean Murphy, Fremont, CA (US); Janice L. Marshall, deceased, late of Sunnyvale, CA (US), by Louise Ann Kruz, legal representative

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/964,271

(22) Filed: Sep. 25, 2001

(51) Int. Cl.[7] ................................. A61B 8/00
(52) U.S. Cl. ..................................... 600/437
(58) Field of Search ................. 600/141, 437, 600/443, 447, 459; 362/26, 31, 33, 572, 604

(56) References Cited

U.S. PATENT DOCUMENTS 4,932,414 A * 6/1990 Coleman et al. ............ 600/439
5,394,871 A * 3/1995 Sauer et al. ................ 600/437
5,538,496 A * 7/1996 Yabe et al. ................. 600/141
5,790,216 A * 8/1998 Inbar et al. .................. 349/83
5,924,988 A    7/1999 Burris et al.

OTHER PUBLICATIONS

Photograph of the Sequoia® 512 Ultrasound System by Acuson Corporation, 1 page (1997).
"Sequoia® 512 Ultrasound System General Applications Reference Manual with Cardiac Option," cover page and pp. 1–19 and 1–20 (Customizing System Lighting) (Jul. 1996).
Information Disclosure Statement, 2 pages (Sep. 25, 2001).

* cited by examiner

Primary Examiner—Francis J. Jaworski

(57) ABSTRACT

The preferred embodiments described herein provide a medical diagnostic ultrasound imaging system with an ambient room light. The medical diagnostic ultrasound imaging system comprises a transducer probe, a beamformer, a processor, and a display device. In one preferred embodiment, an ambient room light is integrated with the display device of the ultrasound system. In another preferred embodiment, the ambient room light is carried by or integrated with an ultrasound imaging system cart that carries some or all of the components of the ultrasound system. Other preferred embodiments are provided, and each of these preferred embodiments can be used alone or in combination with one another.

44 Claims, 6 Drawing Sheets

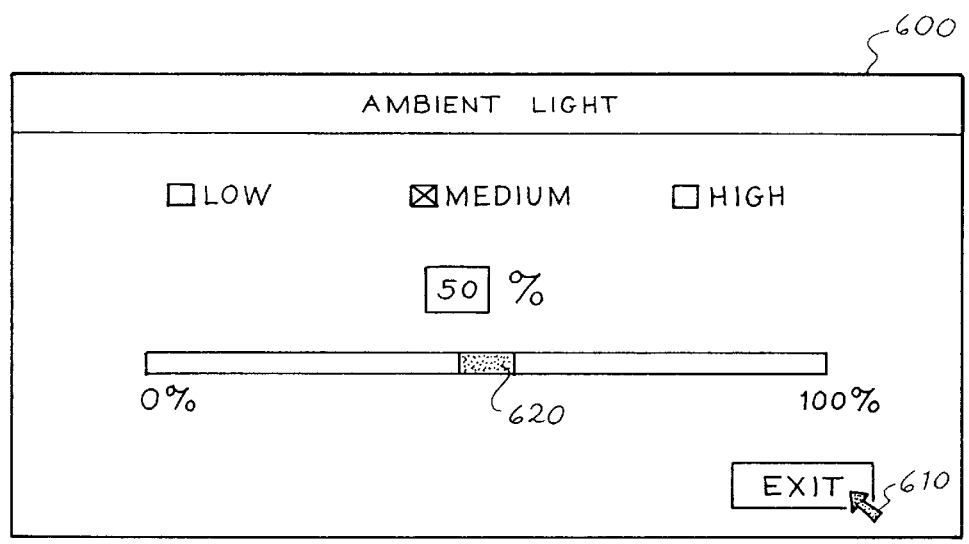
Fig. 6
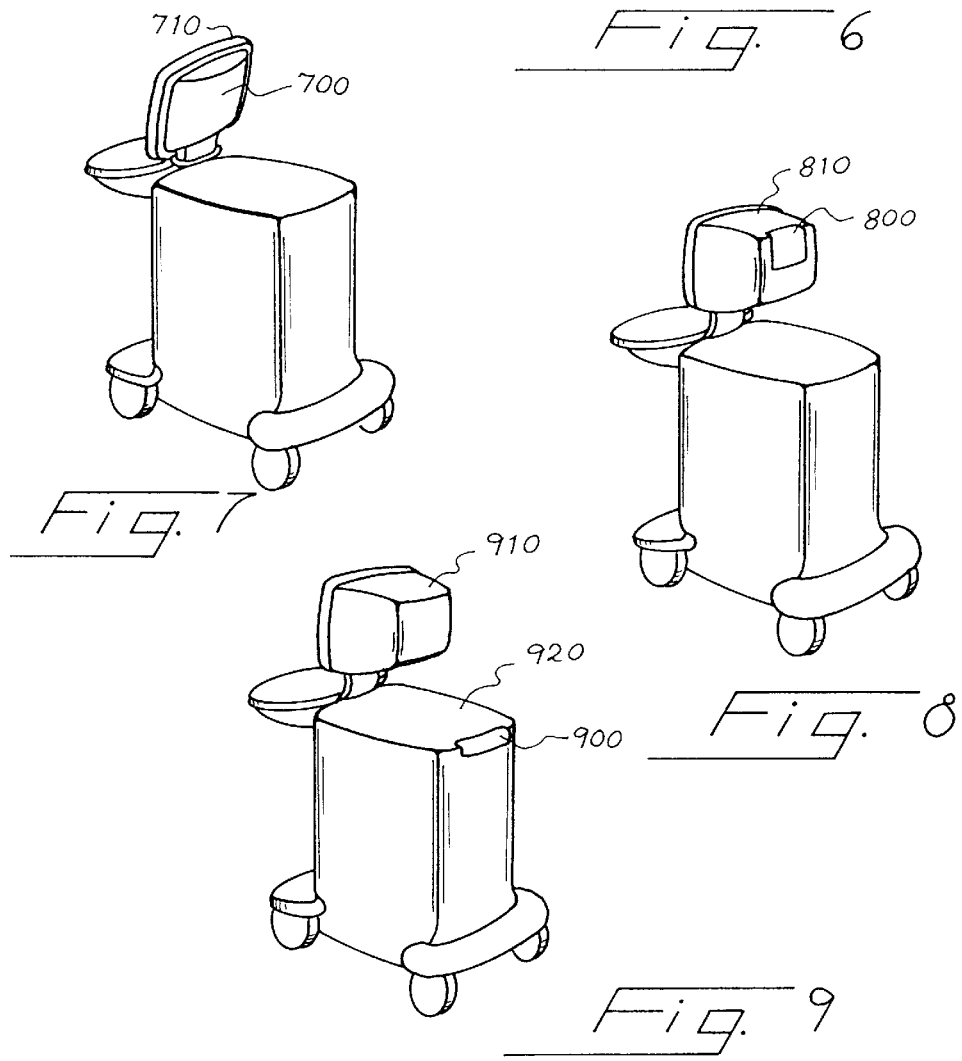
Fig. 7
Fig. 8
Fig. 9

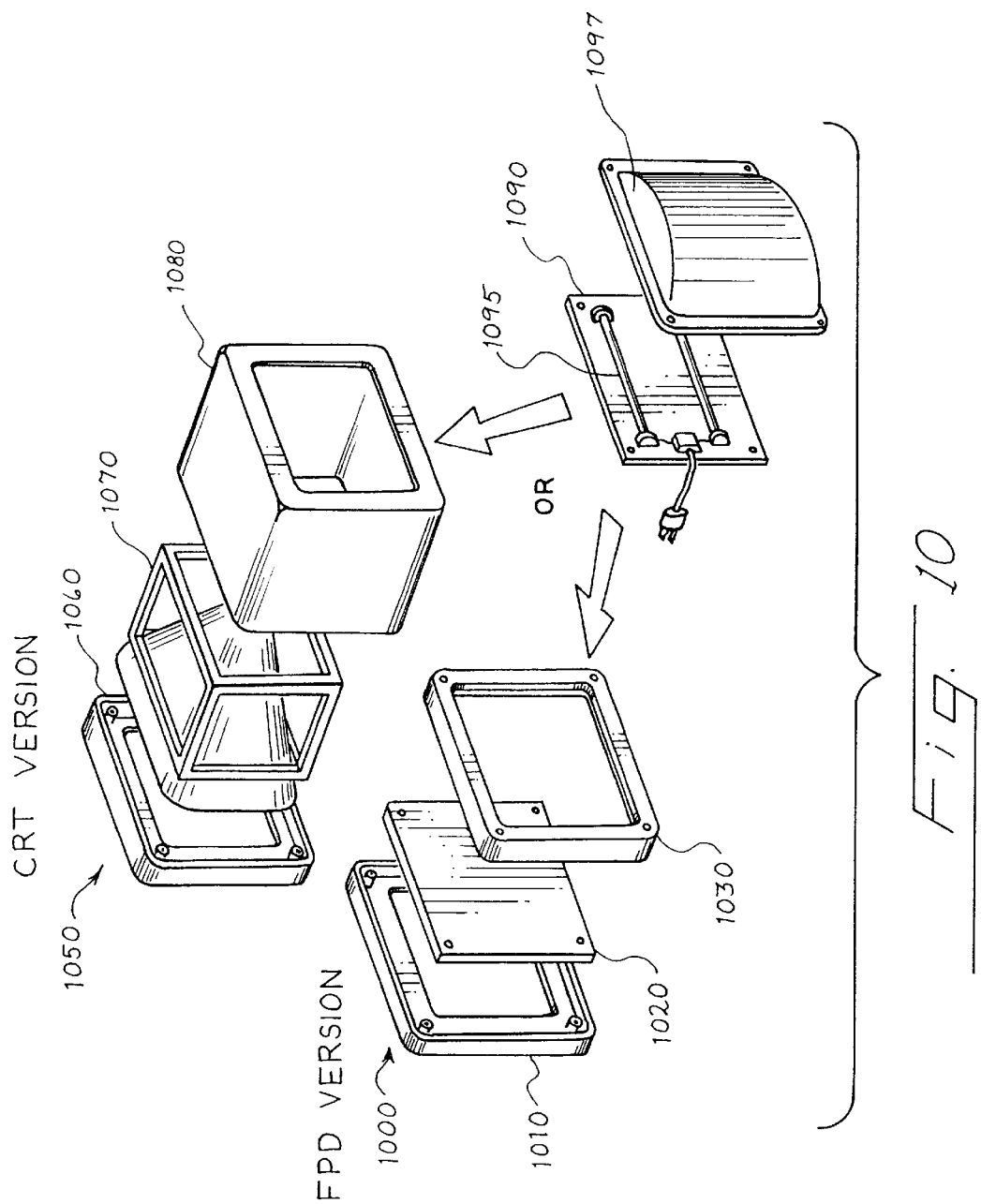

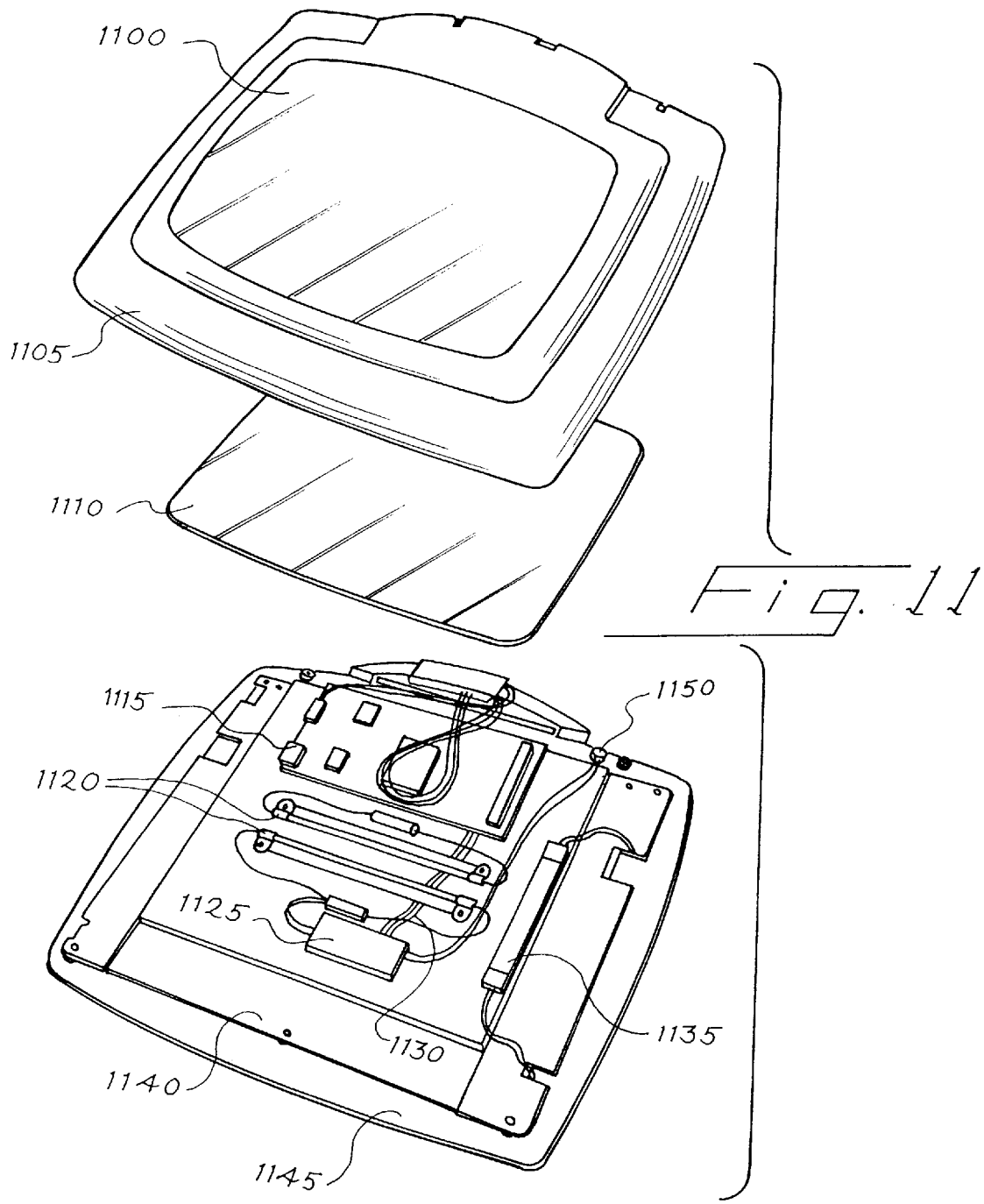

MEDICAL DIAGNOSTIC ULTRASOUND IMAGING SYSTEM WITH AN AMBIENT ROOM LIGHT

BACKGROUND

During an ultrasound examination, a sonographer sitting or standing near an ultrasound imaging system uses one hand to hold an ultrasonic transducer probe in contact with a patient while looking at the ultrasound system's display device. To properly work in the ultrasound environment, it is advantageous to have the ambient room light at a "dim" level. This allows enough light intensity for the user of the ultrasound system to adequately see the patient and the ultrasound system while not having too much light intensity that would interfere with viewing the ultrasound image information on the display device. In addition, it provides a more relaxed environment for the patient and sonographer. In order to achieve the proper balance of ambient room light, the sonographer can adjust the lighting level of the examination room. For example, the sonographer can dim the overhead room lights in the examination room via a wall dimmer switch or, in environments where there is no adjustable lighting (i.e., where overhead room lights are either on or off), a sonographer can turn off the overhead room lights and place a desk lamp in the examination room to cast indirect light throughout the examination room. When the wall dimmer switch or desk lamp is not near the ultrasound system, the sonographer must interrupt the examination of the patient if the sonographer wants to change the lighting level during the examination. Because of this inconvenience, the sonographer may not adjust the lighting level when he would prefer or may work with lighting levels that are not optimum. In addition, if the light were strong enough to illuminate the room, it may be too bright in the user's work area and may conflict with his viewing of the ultrasound image on the display device.

The Sequoia® 512 Ultrasound System by Acuson Corporation has a task light integrated in its cart that illuminates the control panel to provide adequate visual recognition of the controls. A sonographer can adjust the intensity of this light using the control panel; however, even at its highest intensity, the task light is insufficient to adequately illuminate a patient undergoing an ultrasound examination.

There is a need, therefore, for a medical diagnostic ultrasound imaging system that overcomes the disadvantages described above.

SUMMARY

The present invention is defined by the following claims, and nothing in this section should be taken as a limitation on those claims.

By way of introduction, the preferred embodiments described below provide a medical diagnostic ultrasound imaging system with an ambient room light. The medical diagnostic ultrasound imaging system comprises a transducer probe, a beamformer, a processor, and a display device. In one preferred embodiment, an ambient room light is integrated with the display device of the ultrasound system. In another preferred embodiment, the ambient room light is carried by or integrated with an ultrasound imaging system cart that carries some or all of the components of the ultrasound system. Other preferred embodiments are provided, and each of these preferred embodiments can be used alone or in combination with one another.

The preferred embodiments will now be described with reference to the attached drawings.

BRIEF DESCRIPTION OF THE DRAWINGS

FIG. 6 is an illustration of an on-screen control panel of a preferred embodiment having a user interface element for controlling an ambient room light.

FIG. 7 is an illustration of a medical diagnostic ultrasound imaging system of a preferred embodiment having an ambient room light integrated in a flat panel display device.

FIG. 8 is an illustration of a medical diagnostic ultrasound imaging system of a preferred embodiment having an ambient room light integrated in a CRT display device.

FIG. 9 is an illustration of a medical diagnostic ultrasound imaging system of a preferred embodiment having an ambient room light integrated in an ultrasound imaging system cart.

FIG. 10 is an exploded view of a flat panel display device and a CRT display device of a preferred embodiment having an ambient room light.

FIG. 11 is an exploded view of a flat panel display device integrated with an ambient room light of a preferred embodiment.

DETAILED DESCRIPTION OF THE PRESENTLY PREFERRED EMBODIMENTS

Figure 1:
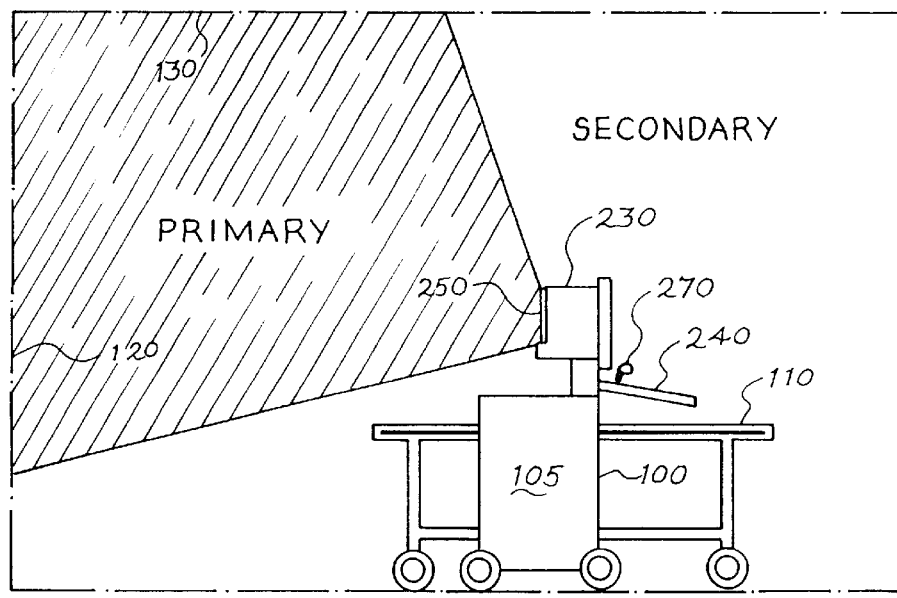
FIG. 1 is an illustration of an ultrasound examination room of a preferred embodiment.

Turning now to the drawings, FIG. 1 is an illustration of an ultrasound examination room of a preferred embodiment. As shown in FIG. 1, a medical diagnostic ultrasound imaging system 100 is positioned next to a patient support surface 110 (here, a gurney), which supports a patient during an ultrasound examination. Instead of being separate components, the patient support surface can be combined with the ultrasound system, as described in "Medical Diagnostic Ultrasound Imaging System with a Patient Support Surface," U.S. patent application Ser. No. 09/964,278, which is being filed on the same day as the present application and is hereby incorporated by reference.

Figure 2:
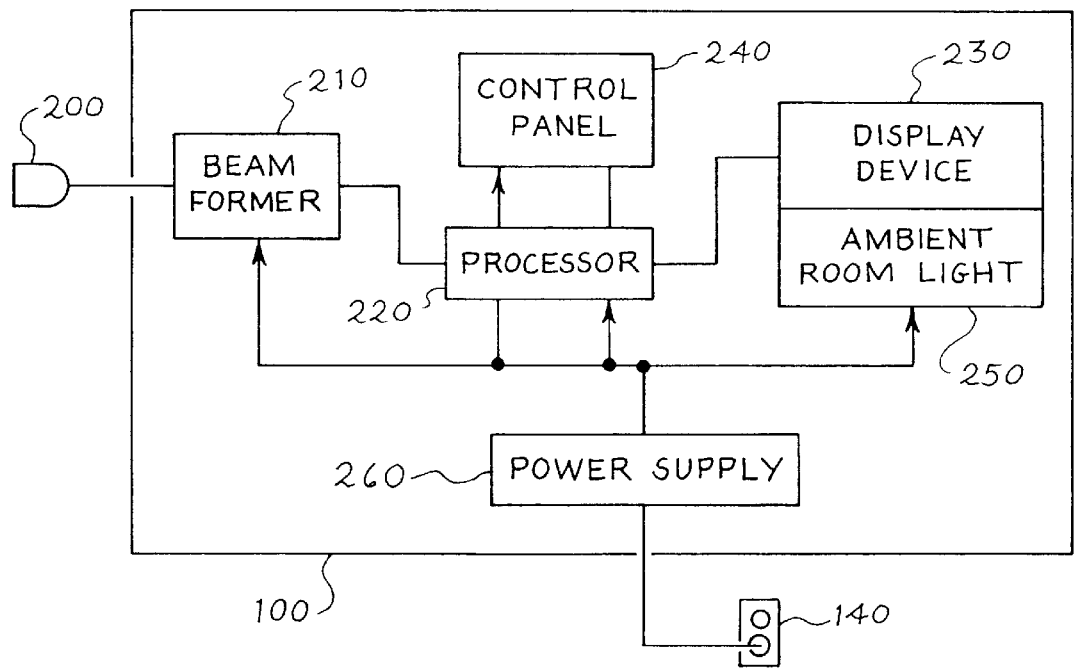
FIG. 2 is a block diagram of components of a medical diagnostic ultrasound imaging system of a preferred embodiment.

FIG. 2 is a block diagram of components of the ultrasound system 100 of FIG. 1. As shown in FIG. 2, the medical diagnostic ultrasound imaging system 100 comprises a transducer probe 200, a beamformer 210 coupled with the transducer probe 200, a processor 220 coupled with the beamformer 210, a display device 230 coupled with the processor 220, and a control panel 240 (e.g., a user interface) coupled with the processor 220. As used herein, the term "coupled with" means directly coupled with or indirectly coupled with through one or more named or unnamed intervening components. The ultrasound system 100 also comprises an ambient room light 250 that is integrated with the display device 230. (As described below, the ambient room light does not necessarily need to be integrated with the display device 230 and can be separate from the display device 230.) The components of the ultrasound system 100 are powered by voltages developed by a power supply 260, which is plugged into an AC outlet 140 in the examination room. While a single power supply 260 is shown in FIG. 2, it should be noted that multiple power supplies can be used. For example, the display device 230 and/or the ambient room light 250 can have its own power supply. In this preferred embodiment, the components of the ultrasound system are carried by a wheeled cart 105.

During an examination, a sonographer contacts the transducer probe 200 with a patient, and the ultrasound system's processor 220 causes the beamformer 210 to apply a voltage to the transducer 200 to cause it to vibrate and emit an ultrasonic beam into the portion of the patient's body in contact with the transducer 200. Ultrasonic energy reflected from the patient's body impinges on the transducer 200, and the resulting voltages created by the transducer 200 are received by the beamformer 210. The processor 220 processes the sensed voltages to create an ultrasound image associated with the reflected signals and displays the image on the display device 230. The control panel 240 can be used, for example, to adjust parameters used in the transmit, receive, and display operations. As used herein, the term "processor" is meant to broadly refer to the appropriate hardware and/or software components of the ultrasound system that can be used to implement the functionality described herein. It should be understood that any appropriate hardware (analog or digital) or software can be used and that the embodiments described herein can be implemented exclusively with hardware. Further, the processor 220 can be separate from or combined with (in whole or in part) other processors of the ultrasound system (including attendant processors), which are not shown in FIG. 2 or described herein for simplicity. Further, it should be noted that the ultrasound imaging system can comprise additional components. Additionally, the ultrasound system can be used with any suitable imaging mode (e.g., B-mode imaging, Doppler imaging, tissue harmonic imaging, contrast agent harmonic imaging, etc.), and the transducer probe 200 can have a transducer of any suitable type (e.g., 1 D, 1.5 D, plano-concave, single element, phased-array, etc.).

As described above, the ultrasound system 100 comprises an ambient room light 250. An ambient room light is a light source that is used to illuminate a patient in an examination room by directing light not at the patient but at a surface in the examination room, such as the ceiling, wall(s), floor, or a screen. Even though the ambient room light is not directed at the patient, the patient is indirectly illuminated by the light reflected from the surface. As shown in FIG. 1, the ambient room light 250 projects "primary light" to the wall 120 and ceiling 130 of the examination room, and the light reflected from these surfaces (the "secondary light") illuminates the patient (and the rest of the room) with a low-to-medium intensity glow. In addition to the ambient room light 250, the ultrasound system 100 can comprise one or more task lights (such as task light 270). In contrast to an ambient room light, a task light is a light source that is directed to a particular "use area" of the ultrasound system. For example, in FIG. 1, the task light 270 is used to illuminate the control panel 240. A task light can also be directed to an area on the ultrasound system that contains a port in which the transducer probe 200 is connected ("a transducer probe port").

Figure 3:
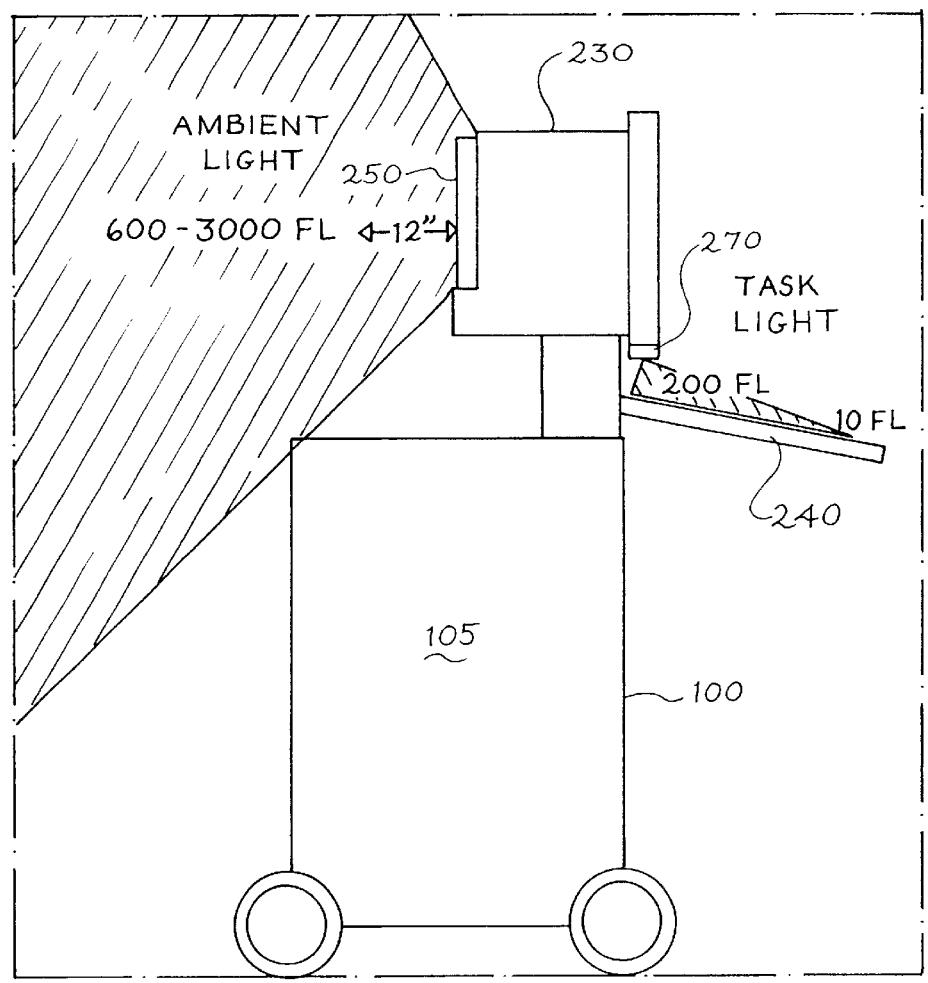
FIG. 3 is an illustration of a medical diagnostic ultrasound imaging system with an ambient room light of a preferred embodiment.

While the task light 270 needs to merely illuminate the control panel 240, the ambient room light 250 needs to properly illuminate the room and the patient. Accordingly, the intensity of the light provided by the task light 270 is much less than the intensity of the light provided by the ambient room light 250. As shown in FIG. 3, the task light 270 preferably provides a light with an intensity between 10 foot lamberts (near the bottom of the control panel 240) and 200 foot lamberts (under the task light 270). Preferably, the ambient room light 250 provides light with an intensity of greater than 200 foot lamberts at a distance of twelve inches from the ambient room light 250. It is especially preferred that the ambient room light 250 provide light with an intensity between 600 and 3,000 foot lamberts at that distance. A suitable intensity can be chosen from this range based on the desired illumination level and size of the examination room.

Figure 4:
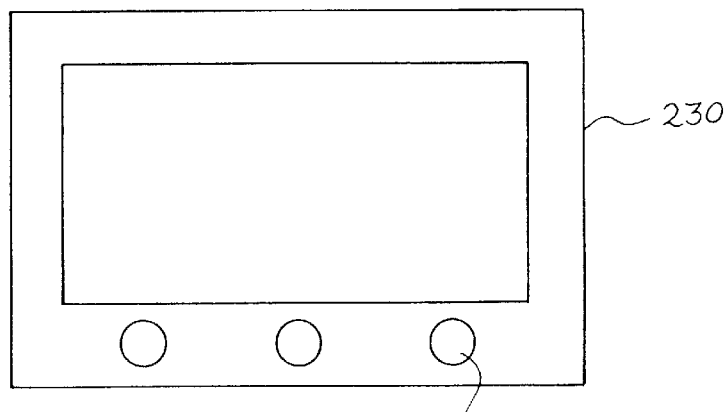
FIG. 4 is an illustration of a display device of a preferred embodiment having a user interface element for controlling an ambient room light.
Figure 5:
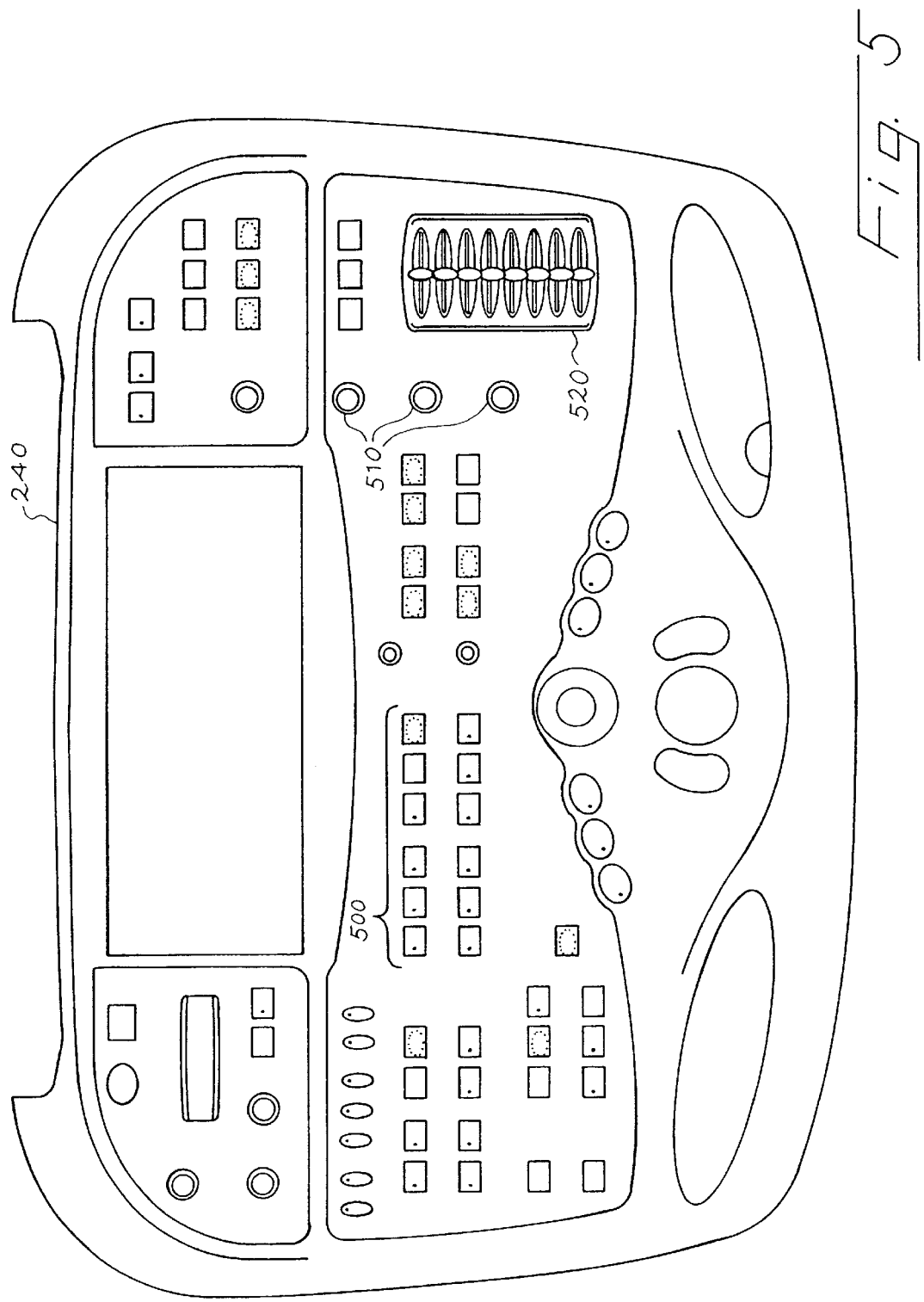
FIG. 5 is an illustration of a control panel of a preferred embodiment having a user interface element for controlling an ambient room light.

Preferably, the ultrasound system 100 comprises a user interface element operative to control the intensity of the light generated by the ambient room light 250. For example, the display device 230 can have a knob 400 (see FIG. 4), or the control panel 240 can have a button 500, knob 510, or slide 520 that controls the intensity of the ambient room light 250. The user-actuatable elements can directly control the ambient room light 250, such as when the knob 400 on the display device 230 is directly connected to a printed circuit board containing the ambient room light 250. Alternatively, the user-actuatable elements can indirectly control the ambient room light 250. For example, turning the knob 510 on the control panel 240 can send a signal to the processor 220, which then can send a signal to a printed circuit board containing the ambient room light 250. In another alternative, an on-screen user interface element is used instead of a physical user interface element. For example, the processor 220 can display an on-screen control panel 600 on the display device 230 to control the ambient room light 250. As shown in FIG. 6, a sonographer can move a pointer 610 on a slide 620 to select an intensity level for the ambient light. The on-screen control panel 600 can also provide user presets (e.g., low, medium, and high) and can also display controls for other system lighting functions (e.g., task lights, keyboard illumination, and output display contrast). With any of these user interface elements, lighting control is convenient for the sonographer because the user interface element can be reached by the sonographer during an ultrasound examination, thereby improving his performance and control of the ultrasound examination.

Turning again to the drawings, FIG. 7 is an illustration of an ultrasound system having an ambient room light 700 integrated into a flat panel display device 710, and FIG. 8 is an illustration of an ultrasound system having an ambient room light 800 integrated into a cathode ray tube (CRT) display device 710. As shown by these perspective views, the ambient room light 700, 800 is located on the ultrasound system in such a way that the light generated by the ambient room light 700, 800 does not interfere with a sonographer's view of the display device 710, 810. Instead of being integrated with a display device 910, an ambient room light 900 can be integrated with a cart 920 carrying the ultrasound imaging system, as shown in FIG. 9. While FIG. 9 shows the ambient room light 900 integrated with the cart 920 between its top and rear surfaces, the ambient room light 900 can be integrated at any location on the cart 920, preferably not at its front surface to avoid the ambient room light 900 being in the sonographer's line of sight to the display device 910. Additionally, instead of being integrated with the cart, the ambient room light can merely be carried by the cart. Further, while FIGS. 7–9 show the ambient room light in a fixed position, the ambient room light can be movable. For example, the ambient room light can take the form of an "eyeball light" having a gimbaled goose neck, allowing a sonographer to tilt and swivel the ambient room light to direct light at a desired location. Of course, any other mechanism to move the ambient room light can be used.

Returning to the drawings, FIG. 10 is an exploded view of a flat panel display device 1000 and a CRT display device 1050 of a preferred embodiment. The flat panel display version 1000 comprises a front bezel 1010, a flat panel display assembly 1020, and a rear cover 1030. The CRT version 1050 comprises a front bezel 1060, a CRT assembly 1070, and a rear cover 1080. A printed circuit board 1090 with florescent lamps 1095 fits into the rear cover 1030, 1080 and plugs into a power outlet receptacle (not shown) in the flat panel display assembly 1020 or the CRT assembly 1070. Alternatively, the printed circuit board 1090 can be wired into the ultrasound system's power supply. A lens 1097 fits oven the rear cover 1030, 1080 to evenly distribute the light generated by the florescent lamps 1095. A more detailed view of the components of the flat panel display version is shown in FIG. 11.

As shown in FIG. 11, the flat panel display device comprises a lens 1100, a rear cover 1105, a diffuser 1110, a video driver board 1115, florescent bulbs 1120, a florescent light inverter 1125, a power cable 1130, a display inverter 1135, a chassis 1140, a front display bezel 1145, and an on/off switch 1150. The lens 1100 is preferably a molded translucent plastic material that has a "frosted" surface on the inside and a smooth to polished surface on the outside. If desired, the outside surface can have a molded-in graphic for product identification, which would be illuminated during use. The inside "frosted" surface provides diffusion by scattering light as it passes through the material, resulting in an even spread of light for better ambient room lighting. It also reduces "hot spots" of light intensity so that the glow of the internal light bulbs is not concentrated in one place. Preferably, this diffusion surface is molded into the lens 1100 for cost and assembly efficiency. Alternatively, it can be an applied spray coating such as a translucent paint. The lens 1100 can also provide color correction of the original light by "filtering" portions of the original light spectrum so that the exiting light achieves the desired color balance. A diffuser 1110 is an optional part depending on the effectiveness of the lens diffusion surface. If the lens diffusion surface does not achieve proper light diffusion, the separate diffuser part 110 can be added to supplement diffusion. The diffuser 1110 can also provide color correction of the original light by "filtering" portions of the original light spectrum so that the exiting light achieves the desired color balance.

The lens 1100 is secured into a rear cover 1105 via screws, snaps, or "heat staking". The rear cover 1105 provides the enclosure on the back half of the flat panel display assembly. Preferably, the rear cover 1105 is made of plastic and is molded in a custom shape to provide all mechanical details for enclosing and capturing the internal details. The rear cover 1105 attaches to a front display bezel 1145 via screws, snaps, or similar fastening methods, covering and enclosing a flat panel display assembly. The flat panel display assembly comprises a chassis 1140, which is the main structural element to which components attach. The chassis 1140 attaches to the front display bezel 1145 via screws or similar hardware. Preferably, the chassis 1140 is made of sheet metal and is custom formed to meet the internal requirements of attachment and structure. The flat panel display "glass" is attached to the chassis 1140 on the front side. The chassis 1140 also supports a video driver board 115, which is a printed circuit board that provides the signal information for the liquid crystal display panel. Here, florescent bulbs 1120 are the primary light source for the ambient light; however, the lamps can be incandescent, LED, or any other technology that meets the electrical requirements of the display. In one preferred embodiment, the florescent bulbs 1120 are approximately 6" long and ¼" in diameter. Additional bulbs can be added to increase the potential light levels. The bulbs 1120 are fixed to the chassis 1140 and are connected via wires to a florescent light inverter 1125. The florescent light inverter 1125 converts DC power to AC in order to drive the bulbs 1120 properly for providing adequate light output. Preferably, the ultrasound system power supply drives the florescent light inverter 1125 via power cable wires 1130. The display inverter 1135 provides the power conversion from the ultrasound system power supply to drive the display.

The chassis 1140 with its assembly of printed circuit boards, lamps, and inverters on its backside and the flat panel display "glass" on its front side is attached to the front bezel 1145 via screws, snaps, or similar fastening methods. If a diffuser 1110 is used, it is preferably placed between the lamps 1120 and the lens 1100. The diffuser 1110 can either attach to the chassis 1140 and be spaced a small distance away from the bulbs 1120 or attach to the rear cover/lens assembly via screws, snaps, or similar fastening methods. The rear cover 1105, with its lens 1100 secured into place, is then placed over the front assembly and fastened together via screws, snaps, or similar fastening methods. This assembly is then attached to the ultrasound system for use.

An on/off switch 1150 connected to the ambient light power circuit can be used to turn the ambient light on and off at the sonographer's choice. Preferably, the switch 1150 is located on the flat panel display assembly where the user can reach it easily. Preferably, the switch 1150 is a "mechanical interlink" switch, which turns the display on when rotated up into the "use" position (vertical +25°, −5° approximately) and turns the display off when rotated to its "rest" position. If the overall ultrasound system power supply powers the ambient light, the ambient light is also turned off if the ultrasound system power is turned off. Instead of an on/off switch 1150, a dimmer control can be used so that the user can control the output intensity. For example, the control can be a physical "knob" (circular rheostat or a rotational potentiometer) located on the flat panel display assembly so that the user would rotate the knob in one direction for brighter and in the other direction for dimmer. The control can also be a "slider" (linear rheostat). Sliding the slider in one direction would make the light brighter and sliding the slider in the other direction would make the light dimmer. Additionally, the brightness intensity controller can be implemented through the ultrasound system's software where the user would use an on-screen control menu to select a preset intensity level or a selected intensity level.

It is intended that the foregoing detailed description be understood as an illustration of selected forms that the invention can take and not as a definition of the invention. It is only the following claims, including all equivalents, that are intended to define the scope of this invention.

What is claimed is:

1. A medical diagnostic ultrasound imaging system with an ambient room light comprising:

a transducer probe;

a beamformer coupled with the transducer probe;

a processor coupled with the beamformer;

a display device coupled with the processor; and an ambient room light integrated with the display device such that the ambient room light directs primary light away from a visual field of the display device and provides secondary light to a patient undergoing an ultrasound examination with the transducer probe.

2. The invention of claim 1, wherein the ambient room light provides light with an intensity sufficient to illuminate the patient.

3. The invention of claim 1, wherein the ambient room light provides light with an intensity greater than 200 foot lamberts at a distance of twelve inches from the ambient room light.

4. The invention of claim 1, wherein the ambient room light provides light with an intensity greater than 600 foot lamberts at a distance of twelve inches from the ambient room light.

5. The invention of claim 1, wherein the ambient room light provides light with an intensity between 600 and 3,000 foot lamberts at a distance of twelve inches from the ambient room light.

6. The invention of claim 1, wherein the medical diagnostic ultrasound imaging system further comprises a task light.

7. The invention of claim 6, wherein the medical diagnostic ultrasound imaging system further comprises a control panel, and wherein the task light is directed to the control panel.

8. The invention of claim 7, wherein the task light provides light at the control panel at an intensity less than 200 foot lamberts.

9. The invention of claim 7, wherein the task light provides light at the control panel at an intensity between 10 and 200 foot lamberts.

10. The invention of claim 6, wherein the medical diagnostic ultrasound imaging system further comprises a transducer probe port, and wherein the task light is directed to the transducer probe port.

11. The invention of claim 1, wherein the medical diagnostic ultrasound imaging system further comprises a control panel and a transducer probe port, and wherein the medical diagnostic ultrasound imaging system further comprises task lights directed to the control panel and the transducer probe port.

12. The invention of claim 1 further comprising a medical diagnostic ultrasound imaging system cart carrying the transducer probe, beamformer, processor, and display device.

13. The invention of claim 1, wherein the ambient room light directs primary light to at least one surface of an examination room in which the medical diagnostic ultrasound imaging system is located, and wherein the secondary light is reflected from the at least one surface.

14. The invention of claim 1 further comprising a user interface element operative to control intensity of light generated by the ambient room light.

15. The invention of claim 14, wherein the user interface element is located on the display device.

16. The invention of claim 14, wherein the medical diagnostic ultrasound imaging system further comprises a control panel, and wherein the user interface element is located on the control panel.

17. The invention of claim 14, wherein the user interface element is displayed on the display device.

18. A medical diagnostic ultrasound imaging system with an ambient room light comprising:
  a medical diagnostic ultrasound imaging system cart carrying:
    a transducer probe;
    a beamformer coupled with the transducer probe;
    a processor coupled with the beamformer; and
    a display device coupled with the processor; and
  an ambient room light carried by the medical diagnostic ultrasound imaging system cart such that the ambient room light directs primary light away from a visual field of the display device and provides secondary light to a patient undergoing an ultrasound examination with the transducer probe.

19. The invention of claim 18, wherein the ambient room light is integrated with the medical diagnostic ultrasound imaging system cart.

20. The invention of claim 18, wherein the ambient room light is positionable by a user performing an ultrasound examination on a patient using the transducer probe.

21. The invention of claim 18, wherein the ambient room light provides light with an intensity sufficient to illuminate the patient.

22. The invention of claim 18, wherein the ambient room light provides light with an intensity greater than 200 foot lamberts at a distance of twelve inches from the ambient room light.

23. The invention of claim 18, wherein the ambient room light provides light with an intensity greater than 600 foot lamberts at a distance of twelve inches from the ambient room light.

24. The invention of claim 18, wherein the ambient room light provides light with an intensity between 600 and 3,000 foot lamberts at a distance of twelve inches from the ambient room light.

25. The invention of claim 18, wherein the medical diagnostic ultrasound imaging system further comprises a task light.

26. The invention of claim 25, wherein the medical diagnostic ultrasound imaging system further comprises a control panel, and wherein the task light is directed to the control panel.

27. The invention of claim 26, wherein the task light provides light at the control panel at an intensity less than 200 foot lamberts.

28. The invention of claim 26, wherein the task light provides light at the control panel at an intensity between 10 and 200 foot lamberts.

29. The invention of claim 25, wherein the medical diagnostic ultrasound imaging system further comprises a transducer probe port, and wherein the task light is directed to the transducer probe port.

30. The invention of claim 18, wherein the medical diagnostic ultrasound imaging system further comprises a control panel and a transducer probe port, and wherein the medical diagnostic ultrasound imaging system further comprises task lights directed to the control panel and the transducer probe port.

31. The invention of claim 18, wherein the medical diagnostic ultrasound imaging system cart comprises a front surface facing a user of the ultrasound system when the user is performing an ultrasound examination on a patient using the transducer probe, and wherein the ambient room light is located at a surface of the medical diagnostic ultrasound imaging system cart other than the front surface.

32. The invention of claim 18, wherein the ambient room light directs primary light to at least one surface of an examination room in which the medical diagnostic ultrasound imaging system cart is located, and wherein the secondary light is reflected from the at least one surface.

33. The invention of claim 18 further comprising a user interface element operative to control intensity of light generated by the ambient room light.

34. The invention of claim 33, wherein the user interface element is located on the display device.

35. The invention of claim 33, wherein the medical diagnostic ultrasound imaging system further comprises a control panel, and wherein the user interface element is located on the control panel.

36. The invention of claim 33, wherein the user interface element is displayed on the display device.

37. A medical diagnostic ultrasound imaging system with an ambient room light comprising:
- a transducer probe;
- a beamformer coupled with the transducer probe;
- a processor coupled with the beamformer; and
- a display device assembly coupled with the processor and comprising:
  - a rear cover with a lens;
  - a front cover coupled with the rear cover;
  - a chassis located between the rear and front covers supporting an ambient room light; and
  - a display device located between the rear and front covers.

38. The invention of claim 37, wherein the display device comprises a flat panel display.

39. The invention of claim 37, wherein the display device comprises a cathode ray tube.

40. The invention of claim 37 further comprising a diffuser located adjacent the lens.

41. The invention of claim 37, wherein the chassis further supports a video driver board.

42. The invention of claim 37, wherein the chassis further supports a display inverter.

43. The invention of claim 37, wherein the chassis further supports a florescent light inverter.

44. The invention of claim 37, wherein the display device assembly further comprises a user interface element operative to control the ambient room light.

* * * * *